(12) United States Patent
Wang et al.

(10) Patent No.: US 6,638,416 B2
(45) Date of Patent: Oct. 28, 2003

(54) HYDROGEN SENSING PROCESS

(75) Inventors: Da Yu Wang, Troy, MI (US); David K. Chen, Rochester Hills, MI (US); Kaius K. Polikarpus, Grand Blanc, MI (US); Walter T. Symons, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 61 days.

(21) Appl. No.: 09/961,661

(22) Filed: Sep. 24, 2001

(65) Prior Publication Data
US 2003/0057109 A1 Mar. 27, 2003

(51) Int. Cl.[7] .............................................. G01N 27/407
(52) U.S. Cl. ..................... 205/775; 204/425; 204/426; 204/427
(58) Field of Search ................. 204/421–429; 205/775, 783.5–785

(56) References Cited

U.S. PATENT DOCUMENTS

| | | | | |
|---|---|---|---|---|
| 3,843,400 A | * | 10/1974 | Radford et al. | |
| 4,183,798 A | * | 1/1980 | Esper et al. | |
| 4,795,533 A | * | 1/1989 | Young et al. | |
| 4,908,118 A | * | 3/1990 | Ammende et al. | |
| 5,064,693 A | * | 11/1991 | Hayakawa et al. | |
| 5,133,857 A | * | 7/1992 | Alberti et al. | |
| 5,194,135 A | * | 3/1993 | Hayakawa et al. | |
| 5,453,172 A | * | 9/1995 | Alberti et al. | |
| 5,507,174 A | | 4/1996 | Friese et al. | |
| 5,529,677 A | | 6/1996 | Schneider et al. | |
| 6,214,209 B1 | | 4/2001 | Gruenwald | |

* cited by examiner

Primary Examiner—T. Tung
(74) Attorney, Agent, or Firm—Jimmy L. Funke

(57) ABSTRACT

A hydrogen sensor and process for measuring hydrogen gas concentrations includes a pump cell and a measuring cell. The pump cell includes a first conducting electrolyte layer having a top and a bottom surface, and an electrode disposed on the top and bottom surfaces, wherein the top electrode is in communication with an unknown concentration of hydrogen gas. The measuring cell includes a second conducting electrolyte layer having a top and a bottom surface, and an electrode disposed on the top and bottom surfaces, wherein the bottom electrode is in communication with a reference gas source. A diffusion-limiting barrier is disposed between the pump cell bottom electrode and the measuring cell top electrode, wherein hydrogen diffusion through the diffusion-limiting barrier is controlled by a Knudsen diffusion mechanism at hydrogen concentrations greater than about 40%.

11 Claims, 7 Drawing Sheets

HYDROGEN SENSING PROCESS

BACKGROUND OF THE INVENTION

To ease pollution, it is advantageous to use hydrogen as the fuel for various mobile and stationary engines, and fuel cells. The source of hydrogen can be from the electrolysis of water, from the transformation of hydrocarbon fuels such as gasoline or natural gas, or the like. The concentration of hydrogen in a fuel gas or the like is an important parameter that is preferably carefully, rapidly and accurately monitored. For example, in hydrogen fuel cells, the concentration of hydrogen is continuously monitored for process control.

The automotive industry has used various gas sensors in automotive vehicles for many years. For example, electrochemical sensors based on polarographic principles have been developed for determining the concentration of oxygen or unburned components in exhaust gases produced by an internal combustion engine or a motor vehicle. These types of oxygen sensors typically include a pump cell and a Nernst cell built, for example, from solid oxide electrolyte materials such as doped zirconia, and linked together through an external electrical circuit. The Nernst cell includes an air reference electrode (or a biased reference electrode) and a sensing electrode with a solid electrolyte therebetween. The pump cell includes a first and second electrode with a solid electrolyte therebetween and a gas chamber with an aperture. The first electrode of the pump cell and the sensing electrode of the Nernst cell are exposed to the gas chamber that receives a representative flow of test gas, such as engine exhaust gas. A controlled electrical potential is applied to the pump cell to pump oxygen into and out of the gas chamber to maintain the electromotive force of the Nernst cell as sensed at the air reference electrode thereof at a desired potential.

To provide for sensing of the oxygen concentration in the test gas, such as by sensing oxygen flux in the gas chamber, the sensor must be maintained in a current limiting range of operation by maintaining the Nernst potential applied to the sensor within a predetermined voltage range. The current limiting range of operation is characterized by a sensor output current that is insensitive to variations in the potential applied to the pump cell. In such a range of operation, the aperture limits gas flux into or out of the gas chamber and sensor output current indicates the maximum flow that can be supported by the concentration in the test gas. If the potential is above the predetermined Nernst voltage range, additional oxygen may be stripped from gas species such as water ($H_2O$) and carbon dioxide ($CO_2$), skewing the relationship between the gas concentration and sensor output current. If the potential is below the predetermined Nernst voltage range, an excess of oxygen is available and sensor output current does not indicate oxygen concentration but rather is a nonlinear function of the gas concentration.

Current sensors such as the oxygen sensors described above are inadequate for determining hydrogen concentration over a wide range of concentrations. For example, zirconia is a solid-state electrolyte material frequently used in the manufacture of oxygen sensors. In these applications, the electrolyte material conducts oxide ions not protons. In contrast, for hydrogen sensing the electrolyte material is a proton-conducting electrolyte, especially in oxygen-deficient atmospheres. However, many of the electrolyte materials used in oxygen gas sensors exhibit poor stability or do not exhibit sufficient conductivity. For example, barium ceria, barium zirconia, strontium ceria, and strontium zirconia are not stable when fuel gas contains water vapor or carbon dioxide. As a result, sensors employing these materials have limited applications, because either the electrolyte materials are instable and have tendency to decompose in the fuel gas environment, or the conductivity of the materials is too low to be practical for sensing applications. Moreover, when the hydrogen concentration approaches 100%, the pump current approaches an infinite number because the gas cell surrounded by the diffusion-limiting barrier becomes a vacuum and the hydrogen has no diffusion limitation into the cell. Thus, it is desirable to have a hydrogen sensing device that is stable, exhibits high conductivity to permit operation at temperatures as low as about 450 to 500° C. and is sensitive to hydrogen concentrations over a wide range (e.g., 0% to 100%).

SUMMARY OF THE INVENTION

A method of measuring a hydrogen concentration in a gas comprises exposing a hydrogen sensor to the gas. The hydrogen sensor includes a pump cell, a measuring cell, and an insulating layer disposed between the pump cell and the measuring cell. The pump cell comprises a first pump electrode exposed to the gas, a second pump electrode in operable communication with a diffusion-limiting barrier, and a first conducting electrolyte disposed between the first and second pump electrodes. The measuring cell comprises a sensing electrode in operable communication with the diffusion-limiting barrier, a reference electrode in fluid communication with a reference gas source and a second conducting electrolyte disposed between the sensing and the reference electrodes. The diffusion-limiting barrier has a pore size sufficient to produce a Knudsen diffusion mechanism at hydrogen concentrations greater than about 40%. The process further includes applying a voltage to the first and the second pump electrodes to form a pump current; diffusing hydrogen molecules across the diffusion-limiting barrier; generating an electromotive force signal between the sensing electrode and the reference electrode; and adjusting the pump current to maintain the electromotive force signal at a predetermined value, wherein the hydrogen concentration is proportional to the pumping current.

In another embodiment, a hydrogen gas sensor comprises a pump cell and a measuring cell. The pump cell comprises a first electrode and a second electrode, and a first conducting electrolyte layer interposed between the first and the second electrode, wherein the first electrode is in fluid communication with a testing gas. The measuring cell, in operable communication with the pump cell, comprises a third and a fourth electrode, and a second conducting electrolyte layer interposed between the third and fourth electrodes, wherein the fourth electrode is in fluid communication with a reference gas. A diffusion-limiting barrier is disposed in fluid communication with the pump cell second electrode and the measuring cell third electrode, wherein the diffusion-limiting barrier has a pore size sufficient to produce a Knudsen diffusion mechanism at hydrogen concentrations greater than about 40%. An insulating layer is interposed between the pump cell and the measuring cell, wherein the insulating layer comprises a via coaxial and in fluid communication with the pump cell second electrode, the diffusion limiting barrier and the measuring cell third electrode.

In another embodiment, a hydrogen sensor comprises means for applying an electrical potential to a pump cell for migrating hydrogen molecules across a diffusion limiting barrier and into a measuring cell, wherein the diffusion limiting barrier comprises a pore size sufficient to produce a Knudsen diffusion mechanism at hydrogen ion concentrations greater than about 40%; and means for maintaining an electromotive force in the measuring cell, wherein the electrical potential is proportional to a concentration difference of the hydrogen molecules between a test gas and a reference gas.

The above described and other features are exemplified by the following figures and detailed description.

BRIEF DESCRIPTION OF THE DRAWINGS

Referring now to the figures wherein the like elements are numbered alike.

DESCRIPTION OF THE PREFERRED EMBODIMENT

The present disclosure is generally directed to a polarographic hydrogen sensor employing at least two electrochemical cells, i.e., at least one pumping cell operable with at least one measuring cell (Nernst cell). The sensor utilizes conducting electrolytes that are stable to other fuel components such as water, carbon monoxide, carbon dioxide, or the like. Moreover, the sensor includes a diffusion-limiting barrier that provides a Knudsen diffusion mechanism to ensure that the hydrogen flux at or near 100% hydrogen concentration will not go infinite.

Figure 1:
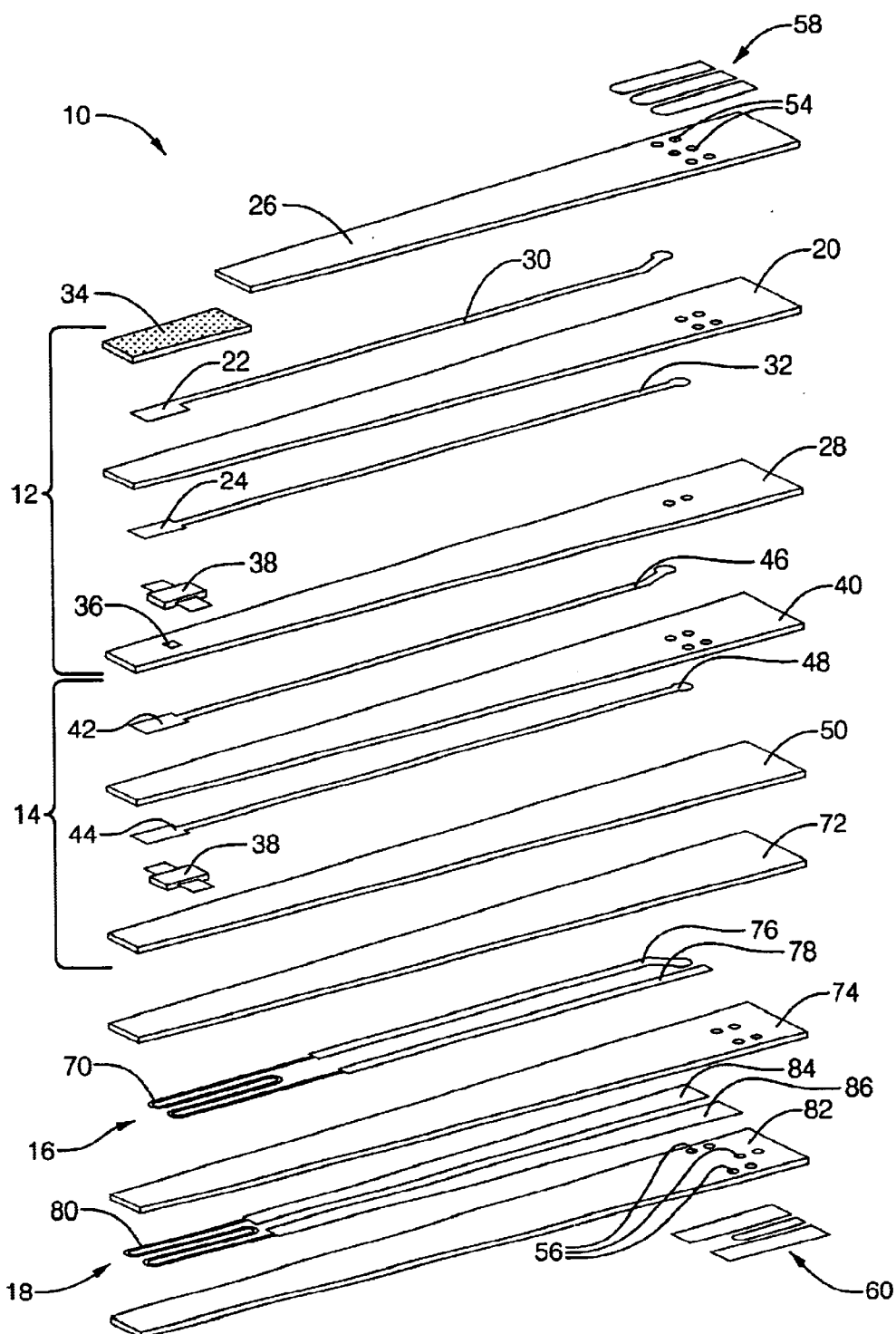
FIG. 1 is an exploded isometric view of a hydrogen gas sensor.

Referring now to FIG. 1, there is depicted a multi-layered hydrogen gas sensor generally designated by reference numeral 10. The hydrogen gas sensor 10 comprises two electrochemical cells: a hydrogen pump cell 12 and a measuring cell 14. As will be described in further detail, insulating layers, which form semi-enclosed chambers, separate the electrochemical cells. Preferably, the hydrogen gas sensor 10 further includes other components, such as a temperature sensor 16, a heater 18, lead gettering layer, ground plane, and/or the like.

The hydrogen pump cell 12 comprises an ionically conductive electrolyte 20, electrodes 22 and 24 disposed on each major surface of the electrolyte 20 and preferably, insulating layers 26 and 28 disposed on sides of electrodes 22, 24 opposite the electrolyte 20. Conductive leads 30, 32 extend from each electrode 22, 24, respectively. Disposed on the exterior side of electrode 22 and adjacent to insulating layer 26 is a porous protection layer 34, which protects the electrode 22 from impurities that cause can poisoning or degradation in electrode sensitivity. Alternatively, the porous protection layer 34 may be integrated into the insulating layer 26. On the other side of the hydrogen pump cell 12, disposed between electrode 24 and insulating layer 28, is a diffusion-limiting barrier 38.

Similar to the hydrogen pump cell 12, the measuring cell 14 (also referred to as the Nernst cell) comprises an ionically conductive solid electrolyte 40. A sensing electrode 42 is disposed on one side of the electrolyte 40 while a reference electrode 44 is disposed on the opposite side of the electrolyte 40. The reference electrode 44 is in fluid communication with a gas channel (not shown), which, during operation, is exposed to reference gas such as air, the sensing gas, or the like.

Optionally, a second diffusion-limiting barrier 52 is disposed between electrode 44 and insulating layer 50. During operation, it is preferred that the second diffusion-limiting barrier 52, if present, be exposed to the reference gas. Conductive leads 46 and 48 are in electrical communication with the sensing electrode 42 and the reference electrode 44, respectively. Insulating layer 28 (shared with the pump cell 12) and insulating layer 50 are disposed on each side of electrodes 42 and 44, respectively, forming a semi-enclosed chamber. Insulating layer 28 further includes via 36, which is coaxial and in fluid communication with the diffusion barrier 38 and electrodes 24, 42. Optionally, the insulating layer 28 is not employed if the voltage drop through the electrolyte is not a factor, such as when the pumping current is small.

As previously discussed, the hydrogen gas sensor 10 may further include other components, such as the temperature sensor 16, and the heater 18 shown in FIG. 1. The temperature sensor 16 comprises resistor circuitry 70 disposed between insulating layers 72 and 74 with conductive leads 76, 78 extending therefrom. The heater 18 comprises heater circuitry 80 disposed between insulating layer 74 (common to the temperature sensor 16) and insulating layer 82 with conductive leads 84, 86 extending therefrom. Heater 18 can be any heater capable of maintaining the electrode end of the sensor 10 at a sufficient temperature to facilitate the various electrochemical reactions therein.

Vias 54 and 56 are disposed at the peripheral major surfaces of the hydrogen gas sensor 10 (insulating layers 26, 82), at the end opposite the electrodes 22, 24, 42, 44, 70, 80. Other vias (not shown) are disposed in the various layers for providing electrical communication to the various conductive leads. Contacts 58 and 60 are electrically connected to the leads 30, 32, 46, 48, 76, 78, 84 and 86 through vias 54 and 56, respectively.

The insulating layers 26, 28, 50, 72, 74 and 82 can comprise a dielectric material such as a metal oxide, e.g., alumina or a similar material, that is capable of inhibiting electrical communication and providing physical protection. Preferably, the insulating layers comprise a material having substantially similar coefficients of thermal expansion, shrinkage characteristics, and chemical compatibility in order to minimize, if not eliminate, delamination and other processing problems. In a preferred embodiment, each insulating layer is fabricated from high purity alumina, (e.g., greater than or equal to about 96 weight % (wt %) alumina) and preferably flux material. The insulating layers may preferably comprises greater than or equal to about 80 wt % alumina and less than or equal to 20 wt % flux material, with greater than or equal to about 90 wt % alumina and less than or equal to about 10 wt % flux material more preferred, and greater than or equal to about 96 wt % alumina and less than or equal to about 4 wt % flux material even more preferred based upon the total weight of the insulating layer composition. The composition of the flux material can be one or more oxides such as silica, lanthanum oxide, alumina, boron oxide, yttria, and the like, as well as combinations comprising at least one of the foregoing flux materials. An exemplary flux material composition comprises, by weight, about 47.5% silica, about 22.5% lanthanum oxide, about 22.5% alumina, about 5% boron oxide and about 2% yttria, based upon the total weight of the flux material.

The electrolyte 20 or 40 can be formed of any material that is capable of permitting the electrochemical redox reaction of hydrogen molecules while inhibiting the passage of exhaust gases. Possible electrolyte materials include materials such as zirconia, ceria, thoria, and the like, as well as a dopant such as calcia, yttria, lanthana, magnesia, alumina, and the like, as well as combinations comprising at least one of the foregoing electrolyte materials. In a preferred embodiment, the electrolyte is formed of yttria doped zirconia. Preferably the zirconia is doped with less than about 8 wt % yttria, with less than about 6 wt % yttria more preferred, based upon the total weight of the electrolyte. Also preferred is zirconia doped with greater than about 4 wt % yttria, with greater than about 5 wt % yttria more preferred, based upon the total weight of the electrolyte. An exemplary yttria doped zirconia electrolyte comprises 5.5 wt % yttria, 3.8 wt % alumina, and 90.7 wt % zirconia. Advantageously, yttria doped zirconia has been found to be stable to contaminants, such as carbon dioxide, carbon monoxide, water, and the like, at temperatures of about $-40°$ C. to about $1,500°$ C.

The electrodes 22, 24, 42, 44 can comprise any metal capable of ionizing hydrogen including, but not limited to, noble metals such as platinum, palladium, gold, osmium, rhodium, iridium and ruthenium; and metal oxides, such as zirconia, yttria, ceria, calcia, alumina, and the like; as well as combinations comprising at least one of the foregoing metals and/or metal oxides. Preferably, the electrodes comprise platinum. The electrodes preferably have porosity sufficient to permit the diffusion of gas molecules without substantially restricting such hydrogen gas diffusion. Typically, the porosity is greater than the porosity of barriers 38 and 52.

With respect to the size and geometry of electrodes 22, 24, 42 and 44, they are generally adequate to provide current output sufficient to enable signal resolution over a wide range of hydrogen concentrations while preventing reduction (electrolysis) of electrolytes 20, 40. Generally, a thickness less than or equal to about 25 micrometers can be employed, with a thickness less than or equal to about 20 micrometers preferred, and less than or equal to about 18 micrometers more preferred. Also preferred is a thickness greater than or equal to about 1 micrometer, with greater than or equal to about 5 micrometers more preferred, and greater than or equal to about 10 micrometers even more preferred. The width of the electrodes is preferably substantially similar to or less than the width of the electrolyte.

The porous protection layer 34 disposed over pump cell electrode 22 can comprise a spinel (e.g., magnesium aluminate), alumina, zirconia, and the like, as well as combinations comprising at least one of the foregoing materials. This porous protection layer 34 preferably comprises a sufficient porosity to permit fluid communication between sensing electrode 22 and the sensing atmosphere as well as provide protection from impurities that cause can poisoning or degradation in electrode sensitivity.

The diffusion-limiting barrier 38 preferably comprises porosity-controlled ceramics, such that the hydrogen gas diffusion can be controlled by a Knudsen diffusion mechanism at hydrogen concentrations greater than about 40 vol% based upon the total gas volume. Thus, a wall-hydrogen gas collision model controls the diffusion of the hydrogen gas, not molecular intercollisions. As a result, the hydrogen flux near or at 100 vol% hydrogen concentration will not go to infinity and high concentrations will therefore be measurable. In one embodiment, the diffusion-limiting barrier 38 comprises about an 1:1 mixture of high purity alumina powder having an average particle size distribution of about 4.5 micrometers to about 5.5 micrometers and a high purity alumina powder having an average particle size of about 0.3 micrometers to about 0.7 micrometers. Preferably, the particle size distributions are Gaussian distributions centered at about 5 micrometers and about 0.5 micrometers, respectively.

Diffusion-limiting barrier 52 provides fluid communication between the reference gas and electrode 44. The diffusion-limiting barrier may be fabricated from any material and has a sufficient porosity to permit the flow of reference gas to contact the electrode 44.

With respect to the other sensor components, e.g., electrodes 22, 24, 42, 44, electrolytes 20, 40 insulating layers 26, 28, 50, 72, 74, 74, 82, temperature resistor circuitry 70, heater circuitry 80, leads 30, 32, 46, 48, 76, 78, 84, 86, vias 54, 56, 36, contacts 58, 60, diffusion-limiting barriers 38, 52, and the like, they are formed using techniques such as tape casting methods, sputtering, punching and place, spraying (e.g., electrostatically spraying, slurry spraying, plasma spraying, and the like), dipping, painting, and the like, as well as combinations comprising at least one of the foregoing techniques, as is appropriate. For example, electrode 22 can be screen printed onto the solid electrolyte 20. Conductive leads 30, 32, 46, 48, 76, 78, 84 and 86, as well as any vias, e.g., 36, 56, 54, are typically formed simultaneously with electrodes. The components are then laid-up in accordance with the particular type of sensor. The sensor is then heat treated to laminate the layers together. Typically, the sensor is heated to a temperature of about $1,400°$ C. to about $1,550°$ C. for a sufficient period of time to fully fire the layers, with a temperature of about $1,450°$ C. to about $1,510°$ C. preferred, for a period of up to about 3 hours or so, with about 100 minutes to about 140 minutes preferred.

For operation of a polarographic sensor, such as the one shown in FIG. 1, an electrical potential of sufficient strength is applied to the pump cell electrodes for redox of hydrogen present between the pump electrode and the electrolyte in such a way, that the measured current is a function of the hydrogen being diffused through the pores of the electrode and gas diffusion-limiting barrier 38. At steady state, the current, I, in the pump cell 12 creates a smaller mole fraction of hydrogen, x, in the chamber relative to the amount of hydrogen in the ambient or reference gas, $x_0$. The measuring cell 14, which has electrode 42 sharing the same semi-enclosed chamber with electrode 24 of the pump cell (through via 36 and diffusion limiting barrier 38) and has its other electrode 44 in fluid communication with the ambient or reference gas, will give an electromotive force (emf), in accordance with the mathematical relationship shown in Equation (1).

$$\text{emf} = \left(\frac{kT}{ne}\right)\ln\left(\frac{x}{x_0}\right), \quad (1)$$

where k is Boltzmann's constant; T is the absolute temperature; n is the number of charges involved in the electrochemical reaction, for hydrogen, n=2.

The relationship between the current of the pump cell and the molar fraction of hydrogen produced depends on the gas-diffusion-limiting barrier 38 and the diffusion mechanism involved. While not wanting to be bound by theory, it is believed that if the mean free path of the gas is smaller than the pore sizes of the aperture (the gas molecular diffusion mechanism), the pump current is controlled by Fickian diffusion (Fick's first law), and the bulk flow of the gas will be equal to the current. The relationship can be described mathematically as shown in Equation (2).

$$I = -(ncFDA)\left(\frac{\partial x}{\partial y}\right) + Ix, \quad (2)$$

with a solution of, $$I = \left(\frac{ncFDA}{L}\right)\ln\left(\frac{1-x}{1-x_0}\right), \quad (3)$$

where c is total molar concentration, F is Faraday constant, D is hydrogen diffusion constant based on molecular gas diffusion, A is the effective diffusion cross sectional area, and L is the effective diffusion length of the gas-diffusion-limiting aperture. However, if $x_0$ is small, the bulk flow contribution can be ignored in Equation (2) and the solution is simplified as shown in Equation (4).

$$I = -\left(\frac{ncFDA}{L}\right)(x_0 - x). \quad (4)$$

In contrast, if the mean free path of molecular hydrogen gas is larger than the pore sizes of the diffusion-limiting barrier 38, there is no bulk flow contribution to the current in Equation (2) and the solution is the same as expressed in Equation (4), with the exception that different diffusion constants will be required. Gas diffusion under these conditions is controlled by the Knudsen diffusion mechanism where molecules of hydrogen are just as likely to hit the walls within the diffusion-limiting barrier 38 as they are to hit each other. As a result of the Knudsen diffusion of hydrogen, the hydrogen flux near or at 100% hydrogen concentration will not go to infinite.

The applied voltage V, which drives the current I, is equal to:

$$V = IR + \eta_a + \eta_c, \quad (5)$$

where R is the electrolyte resistance, and $\eta_a$ and $\eta_c$ are the anodic and cathodic overpotentials, respectively.

When current is small (defined by the size and geometry of the electrode, e.g., less than about 0.2 milliamps for a 7 square millimeter electrode), Equation (5) can be defined by Equation (6), and consequently, the applied voltage linearly tracks on the emf of the pump cell 12:

$$V = -\left(\frac{kT}{ne}\right)\ln\left(\frac{x}{x_0}\right). \quad (6)$$

Figure 2:
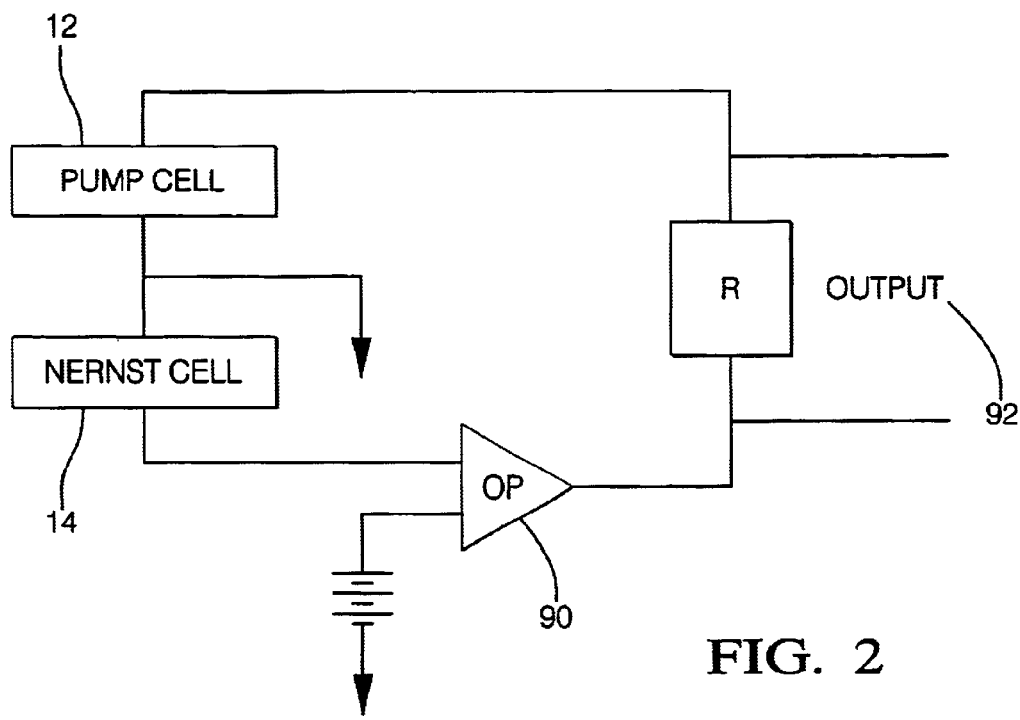
FIG. 2 is an electrical circuit diagram in schematic form of a hydrogen gas sensor.

Referring now to FIG. 2, there is shown an electrical circuit diagram in schematic form of a hydrogen gas sensor. The pump cell 12 and measuring cell 14 are operated with an electronic driver suitable for producing an output signal. Preferably, the electronic driver comprises an operational amplifier 90. The reference voltage for the operational amplifier 90 can be controlled at about 0.2 to about 1.1 volts (V). The voltage applied to the amplifier 90 can be a constant value or variably adjusted with the pump current. An output signal 92 is generated as a function of voltage drop resistance. The polarity of the reference voltage depends on the reference gas chosen for exposure to the reference electrode 44. For example, the polarity will be positive (as shown in FIG. 2) if ambient air is chosen as the reference gas. In contrast, the polarity is negative if the sensing atmosphere is chosen as the reference gas.

EXAMPLES

Example 1

In this example, a hydrogen gas sensor was constructed in accordance with FIG. 1. Green ceramic tapes of 5.5 weight percent yttria doped zirconia (electrolyte) and of alumina (insulating layer) were separately mixed with binders, plasticizers, solvents, and roll-milled into a slurry. The slurry was then cast into tapes as electrolyte and insulating layers, respectively, by doctor blade type casting methods. Platinum inks were screen printed onto the tapes in the structure as shown in FIG. 1 to form platinum electrodes. All of the electrodes had an area of 7 square millimeters ($mm^2$). The porous protection layer was screen printed onto the tapes. The coating was made of a mixture of alumina and yttria doped zirconia powder having a porosity sufficient to provide protection to the underlying electrode but not limit the flow of gas to the electrode. Likewise, the diffusion-limiting barriers were screen printed with carefully controlled dimensions. The diffusion-limiting barrier was fabricated using a 1:1 mixture of high purity alumina with a first particle size distribution of 4.5 microns to 5.5 microns and a second particle size distribution of 0.3 microns to 0.7 microns. The median particle sizes of the first and second distributions were about 5.0 microns and 0.5 microns, respectively. The width of the barrier layer varied from 1 to 4.7 millimeters (mm) with an overall length of 1.25 mm. After thermal lamination of the various components, the sensor was fired at 1,450° C. for two hours.

As previously discussed, the top cell functions as the pump cell while the bottom cell functions as the measuring cell (Nernst cell) with its bottom electrode connected to a gas aperture or channel which is exposed to a sensing atmosphere gas. The diffusion-limiting barriers were used to control the value of the limiting pump current. The temperature of the sensor was manually controlled to about 500° C.

The hydrogen gas sensor was exposed to different mixtures of nitrogen, oxygen, carbon dioxide, and hydrogen modulated by gas flow meters. The total gas flow rates were fixed at one liter per minute. The mixed gases first passed through a bubbler to control the humidity level. The wattage for the sensor heater was increased from 7.8 watts (W) to 20 W as the hydrogen concentration was increased from 0% to 100%.

Figure 3:
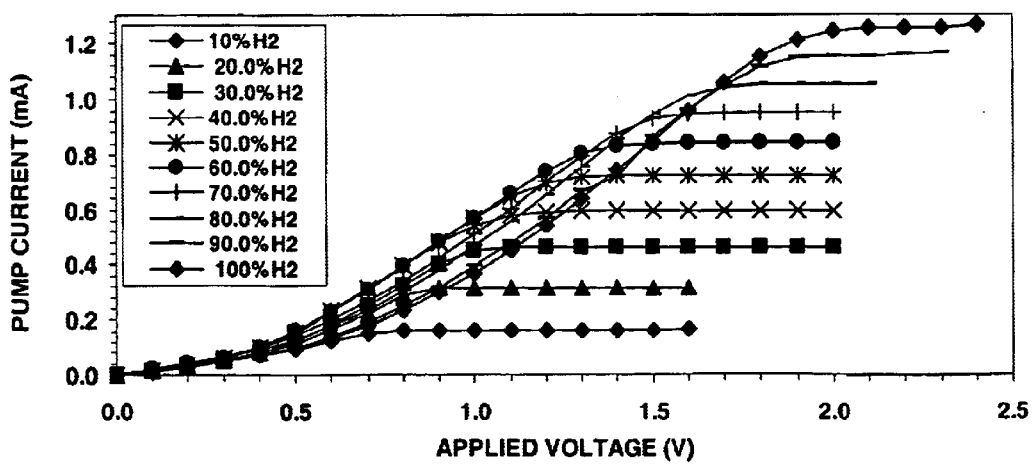
FIG. 3 is a graph illustrating current as a function of applied voltage for hydrogen concentrations varying from 10% to 100%.
Figure 4:
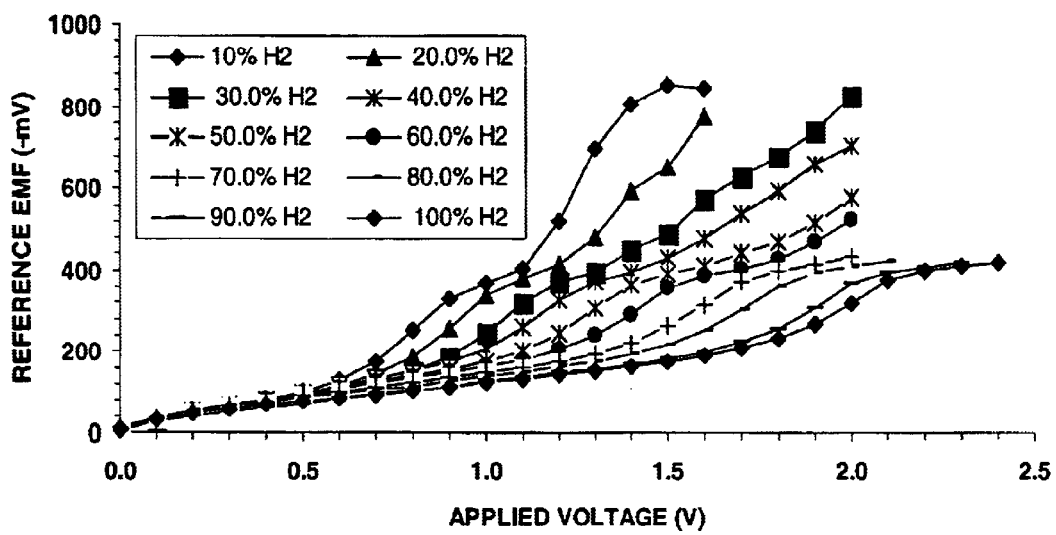
FIG. 4 is a graph illustrating emf as a function of applied voltage for hydrogen concentrations varying from 10% to 100%.

Referring now to FIGS. 3 and 4, the hydrogen sensor was exposed to hydrogen gas concentrations from 10 vol % to 100 vol %. Due to the high thermal conductivity of hydrogen, the sensor temperature varied from 486° C. to 476° C. as the hydrogen concentration was increased from 10% to 100%.

FIG. 3 graphically illustrates the current as a function of applied voltage for the various gas mixtures whereas FIG. 4 graphically shows the corresponding emf values for the different gas mixtures. The shifting of the slope location observed in FIG. 3 is due to the sensor temperature drop because of the higher thermal conductivity of the hydrogen. The data clearly demonstrates the sensitivity of the sensor to varying hydrogen concentrations of 10 vol % to 100 vol %. Each 10 vol % interval of hydrogen concentration exposed to the sensor resulted in a pump current change of at least about 0.1 milliAmp (mA) intervals or more as a function of the applied voltage once a plateau of the pump current was observed.

Figure 5:
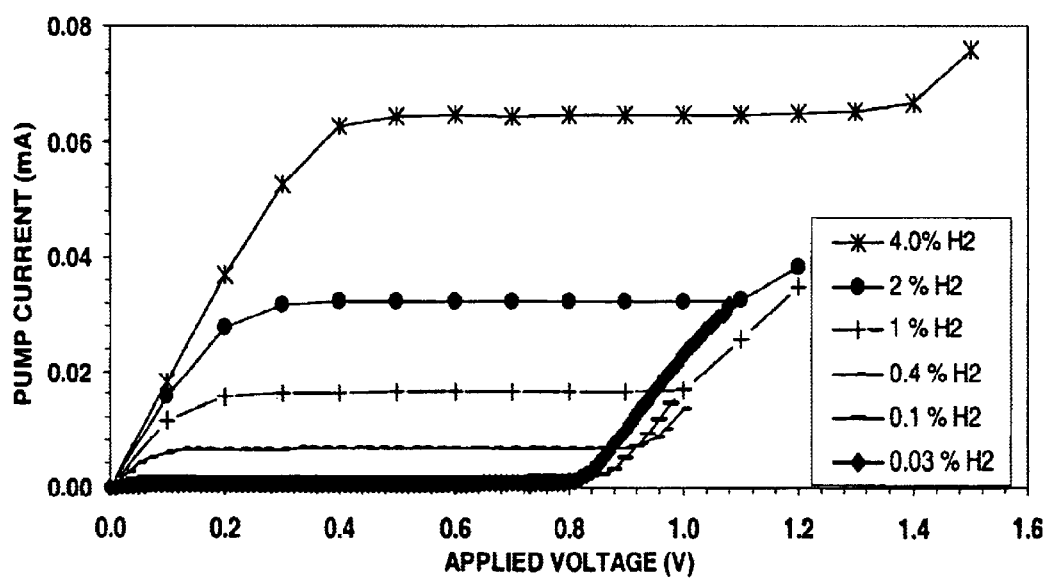
FIG. 5 is a graph illustrating current as a function of applied voltage for hydrogen concentrations varying from 0.03% to 4%.
Figure 6:
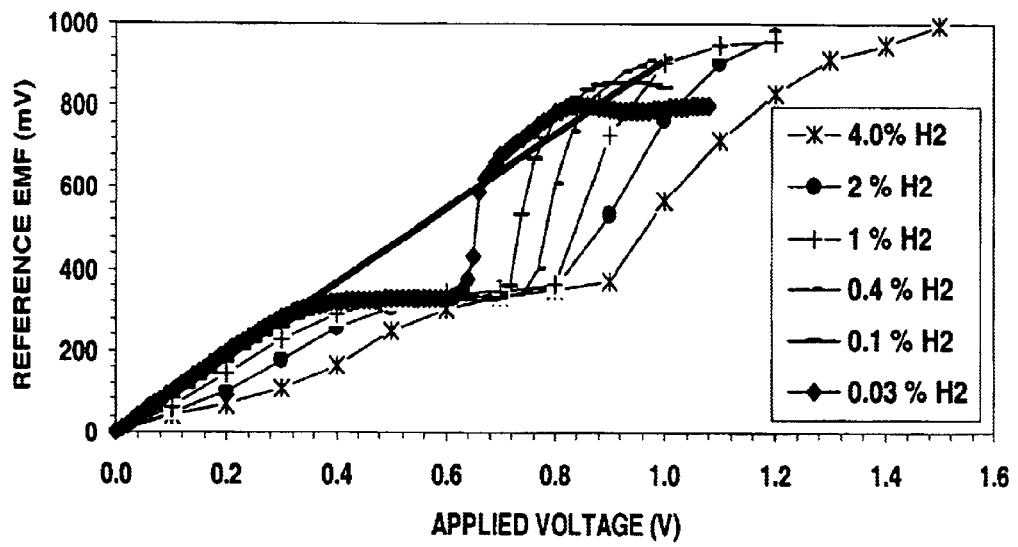
FIG. 6 is a graph illustrating emf as a function of applied voltage for hydrogen concentrations varying from 0.03% to 4%.

FIGS. 5 and 6 graphically illustrate the current and emf sensitivity as a function of applied voltage for hydrogen gas concentrations from 0.03 vol % to 4 vol %. The temperature of the hydrogen gas sensor varied from 491° C. to 499° C. as the hydrogen concentration was increased from 0.03 vol % to 4 vol %. The solid line shown in FIG. 6 represents the theoretical fitting curve assuming that the contribution from IR is ignored (as determined by Equation (6)). As observed, the data is approaching the theoretical fitting curve as the hydrogen concentration becomes smaller, i.e., the limiting current becomes smaller. When the concentration reaches 0.03% the data almost fits the theoretical curve except for an emf deviation between about 320 millivolts (mV) and about 600 mV and a final departure from the fitting curve at large applied voltages where current rises beyond the limiting current plateau (see FIG. 5).

Figure 7:
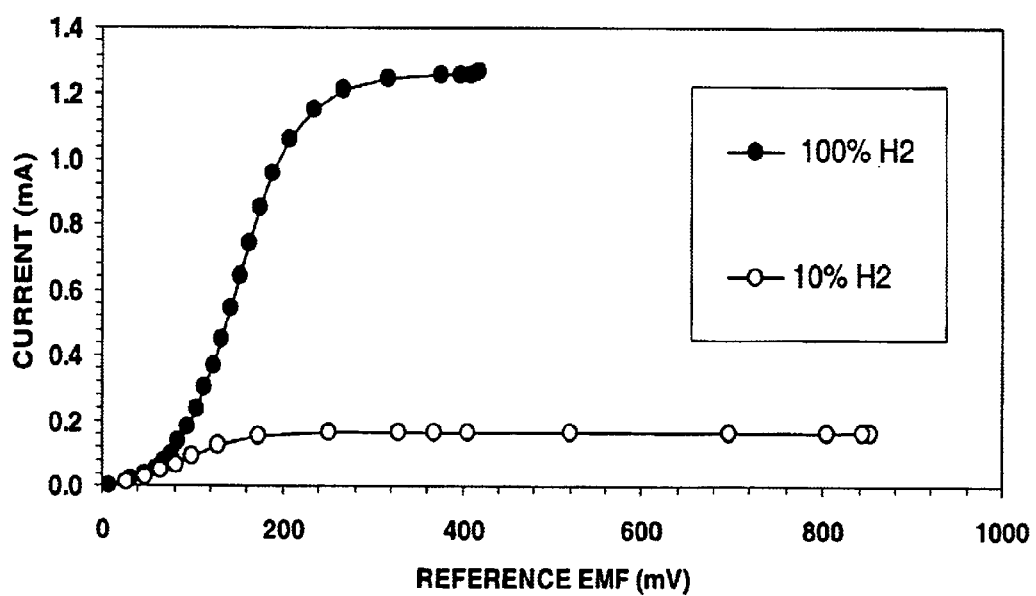
FIG. 7 is a graph illustrating current as a function of emf for hydrogen concentrations of 10% and 100%.
Figure 8:
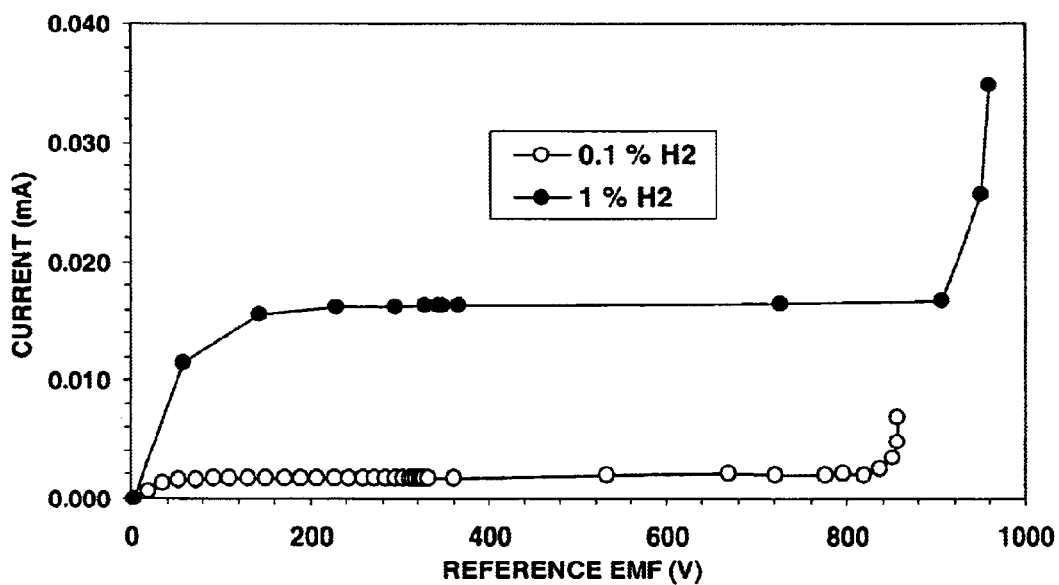
FIG. 8 is a graph illustrating current as a function of emf for hydrogen concentrations of 0.1% and 1%.

FIG. 7 graphically illustrates current as a function of emf based on the results presented in FIGS. 3 and 4. For clarity, only the data of the hydrogen concentrations at 10% and 100% are presented. Similarly, FIG. 8 graphically illustrates the current as a function of emf based on the results presented in FIGS. 5 and 6. Again, for clarity, only the data of the hydrogen concentrations at 0.1% and 1% are presented in FIG. 8. As shown in FIGS. 7 and 8, the pump current reaches a plateau value between the emf values of 300 mV and 800 mV, even for a concentration of 100% hydrogen.

Figure 9:
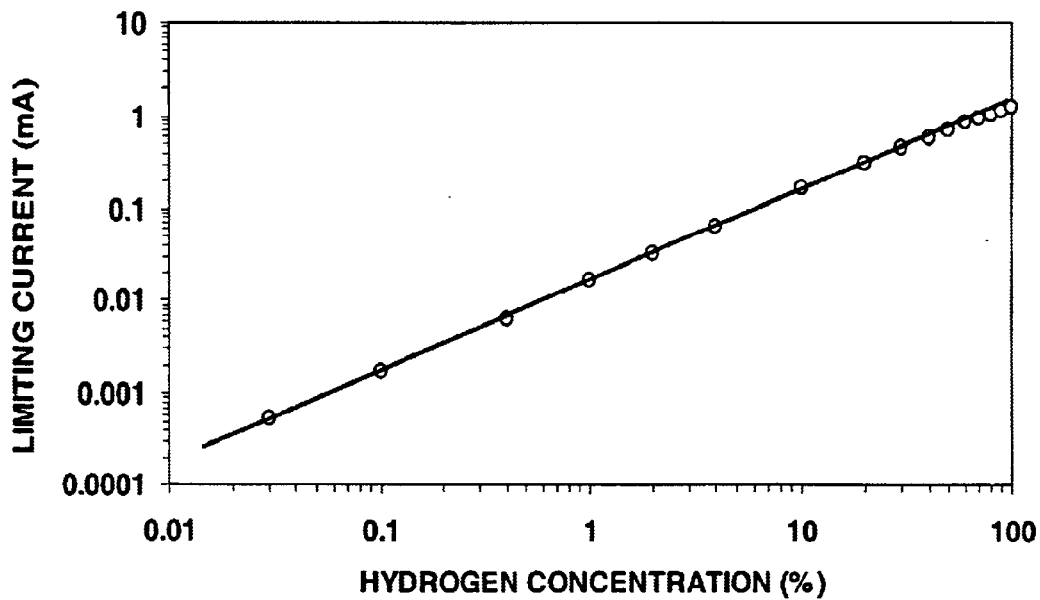
FIG. 9 is a graph illustrating limiting current as a function of hydrogen concentration in a log-log scale.
Figure 10:
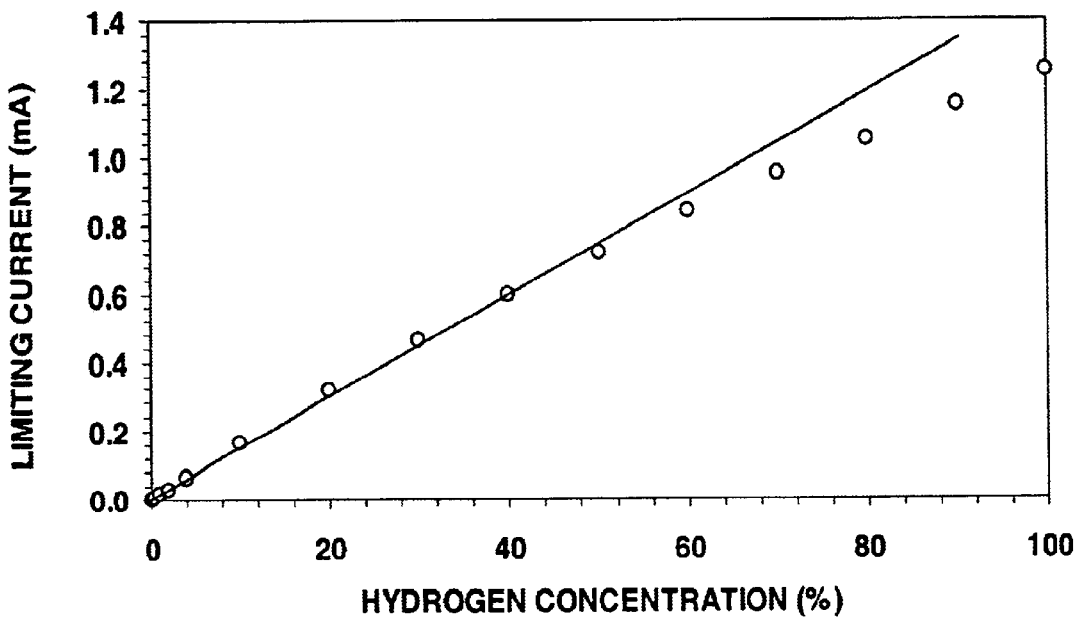
FIG. 10 is a graph illustrating limiting current as a function of hydrogen concentration in a linear scale.

FIG. 9 graphically illustrates a log-log plot of limiting current as a function of hydrogen concentration. FIG. 10 illustrates the same data in a linear scale. The limiting current was determined from the current values obtained at the emf value of 350 mV (shown in FIGS. 7 and 8) for the respective hydrogen concentrations. FIGS. 9 and 10 demonstrate a linear response behavior for hydrogen concentrations from 0.03% to about 40% based on the limiting current. The non-linearity for hydrogen concentrations greater than 40% can be attributed to a shift of the controlling gaseous diffusion mechanism, i.e., gas molecular dynamics or Knudsen diffusion. At hydrogen concentrations lower than about 40%, the diffusion mechanism is primarily controlled by gas molecular dynamics. At hydrogen concentration greater than 40%, the mean free path of hydrogen diffusion increased and a Knudsen diffusion mechanism became the dominant diffusion mechanism.

A factor of two is observed for the limiting currents measured at the same concentration of hydrogen versus oxygen. In air (21% oxygen), the hydrogen sensor has a limiting current of 0.169 millli amps (mA). As shown in FIG. 10, a hydrogen concentration of the same concentration, i.e., 21% hydrogen produces a limiting current of 0.330 mA. This is reasonable since hydrogen diffusivity is four times larger than that of oxygen and carries half the charge of oxygen during the electrochemical reaction.

Example 2

Figure 11:
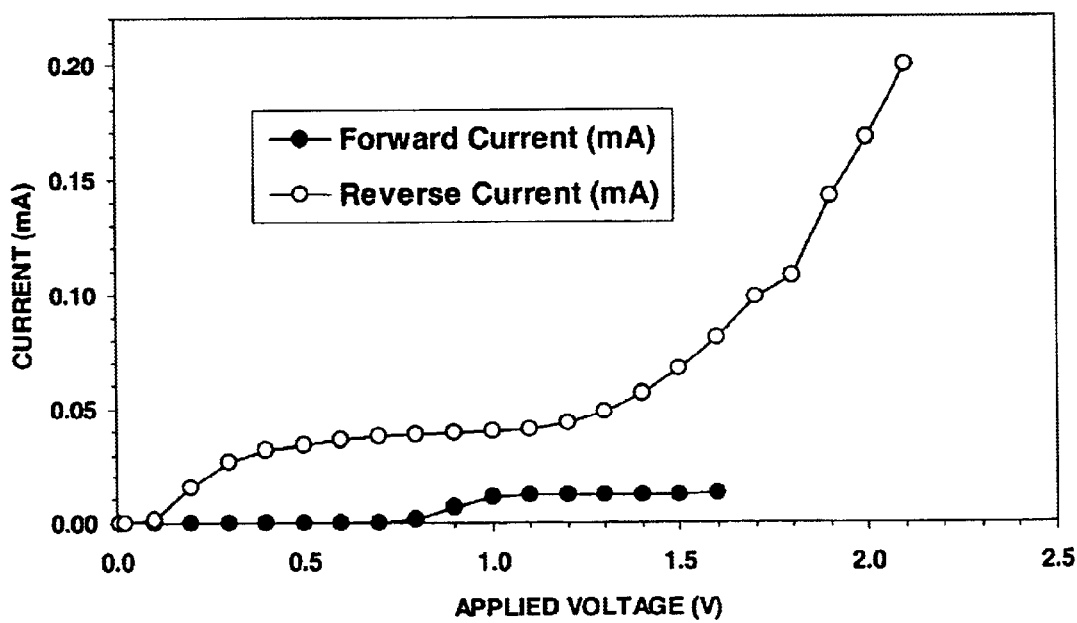
FIG. 11 is a graph illustrating forward and reverse current as a function of applied voltage in a nitrogen gas environment.
Figure 12:
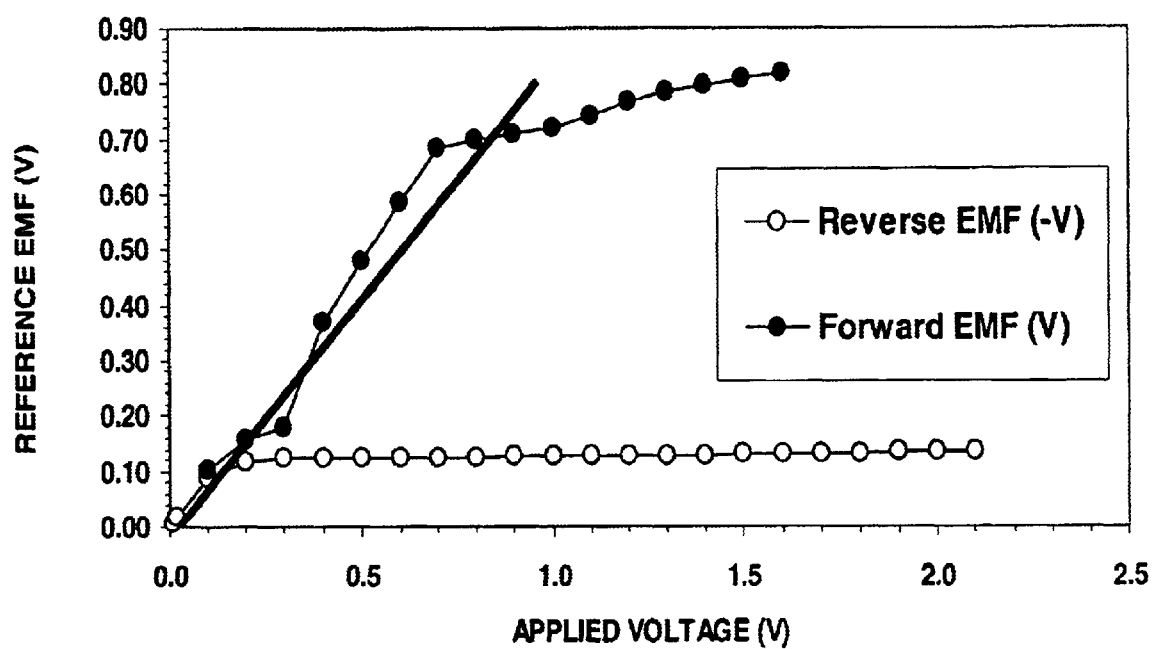
FIG. 12 is a graph illustrating forward and reverse emf as a function of applied voltage in a nitrogen gas environment.

In this example, a hydrogen sensor was constructed as in Example 1 and operated in a wet-nitrogen atmosphere. The sensor was operated at 500° C. with a gas flow rate of 1 liter per minute. When operated in the wet-nitrogen environment, the forward- and reverse-polarity pump currents and the corresponding emf data were plotted against the applied voltages as shown in FIGS. 11 and 12. The forward polarity is defined with the negative electrode assigned to the semi-enclosed chamber pump electrode. As shown in FIG. 11, the forward current-voltage curve plateaus at about 0.4 volts, which represents the dissociation of humidity (1.4% of gas composition). The residual oxygen concentration in the nitrogen gas is estimated to be less than 25 parts per million (ppm). The solid line shown in FIG. 12 represents the theoretical fitting curve assuming IR contribution can be ignored (as determined by Equation (6)). As can be seen in this figure, the fitting of the data is good with the exception of a small deviation at an emf of about 180 mV and a final departure from the fitting curve at large applied voltages.

It should be noted that the pumping current capacity is lower than that shown in Example 1. The lower pump current results since the amount of oxygen carried by nitrogen as an impurity is less than about 25 parts per million, wherein the majority of the oxygen is carried by humidity. Moreover, the presence of hydrogen eliminates most of the available oxygen. Consequently, the amount of oxygen is insufficient to support the limiting current levels first observed in Example 1. While not wanting to be bound by theory, it is believed that a reason for this phenomena is that local proton conduction is occurring at least at the electrode. Surprisingly, the presence of hydrogen molecules at high concentrations did not reduce the yttria doped zirconia electrolyte.

Advantageously, the hydrogen sensor is sensitive to hydrogen concentrations of 0% to 100%. The source of hydrogen can be from a hydrogen gas or a hydrogen containing gas that generates hydrogen upon exposure to the electrodes. For example, exposing the sensor to a hydrocarbon such as methane generates, by dehydrogenation, a source of hydrogen. In this manner, the concentration of the methane gas can be monitored. Moreover, the hydrogen sensor employs the use of materials that are stable from contact with water, carbon monoxide, carbon dioxide, or the like and can be operated at temperatures as low as about 450° C. to about 500° C.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of measuring a hydrogen concentration in a gas, the method comprising:

exposing a hydrogen sensor to the gas, the hydrogen sensor comprising a pump cell, a measuring cell, and an insulating layer interposed between the pump cell and the measuring cell, wherein the pump cell comprises a first pump electrode exposed to the gas, a second pump electrode in operable communication with a diffusion-limiting barrier, and a first conducting electrolyte interposed between the first and second pump electrodes, wherein the measuring cell comprises a sensing electrode in operable communication with the diffusion-limiting barrier, a reference electrode in fluid communication with a reference gas source and a second conducting electrolyte interposed between the sensing and the reference electrodes, and wherein the diffusion limiting barrier has a pore size sufficient to produce a Knudsen diffusion mechanism at hydrogen concentrations greater than about 40%;

applying a voltage to the first and the second pump electrodes to form a pump current;

diffusing hydrogen molecules across the diffusion-limiting barrier;

generating an electromotive force signal between the sensing electrode and the reference electrode; and adjusting the pump current to maintain the electromotive force signal at a predetermined value, wherein the hydrogen concentration is proportional to the pumping current.

2. The method according to claim 1, wherein the first and second conducting electrolytes comprise a composition consisting essentially of yttria, alumina and zirconia.

3. The method according to claim 2, wherein the yttria comprises about 4 weight percent to about 8 weight percent based upon a total weight of the composition.

4. The method according to claim 1, wherein the measuring cell operates as a Nernst cell.

5. The method according to claim 1, wherein the hydrogen sensor is capable of measuring concentrations of hydrogen in the gas mixture from greater than 0% to 100%.

6. The method according to claim 1, wherein the diffusion-limiting barrier comprises a mixture of alumina having a first particle size distribution of about 4.5 micrometers to about 5.5 micrometers and a second particle size distribution of about 0.3 micrometers to about 0.7 micrometers.

7. The method according to claim 6, wherein the mixture comprises about 1 part of the first particle size distribution and about 1 part of the second particle size distribution.

8. The method according to claim 1, further comprising diffusing hydrogen molecules across the diffusion-limiting barrier, wherein the diffusion of the hydrogen molecules is controlled by a molecular intercollision mechanism.

9. The method according to claim 1, wherein the gas comprises a hydrocarbon.

10. The method according to claim 1, wherein the second pump electrode is disposed on the diffusion limiting barrier.

11. The method according to claim 1, wherein the diffusion limiting barrier controls a limiting pump current.

* * * * *